(12) United States Patent
Puckette et al.

(10) Patent No.: US 7,928,267 B1
(45) Date of Patent: Apr. 19, 2011

(54) PHOSPHITE CONTAINING CATALYSTS FOR HYDROFORMYLATION PROCESSES

(75) Inventors: Thomas Allen Puckette, Longview, TX (US); Yun-Shan Liu, College Station, TX (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 12/489,029

(22) Filed: Jun. 22, 2009

(51) Int. Cl.
*C07C 45/50* (2006.01)
*B01J 31/00* (2006.01)
*B01J 27/185* (2006.01)

(52) U.S. Cl. .................... 568/454; 502/166; 502/213
(58) Field of Classification Search .............. 568/454; 502/166, 213
See application file for complete search history.

(56) References Cited

U.S. PATENT DOCUMENTS

| | | | |
|---|---|---|---|
| 4,348,495 A * | 9/1982 | Buysch et al. | 524/117 |
| 4,381,359 A * | 4/1983 | Idel et al. | 524/117 |
| 4,599,206 A | 7/1986 | Billig et al. | |
| 4,608,239 A | 8/1986 | Devon | |
| 4,668,651 A | 5/1987 | Billig et al. | |
| 4,835,299 A | 5/1989 | Maher et al. | |
| 4,873,213 A | 10/1989 | Puckette et al. | |
| 4,912,155 A | 3/1990 | Burton | |
| 5,298,541 A | 3/1994 | Bohshar et al. | |
| 5,712,403 A | 1/1998 | Sato et al. | |
| 5,744,649 A | 4/1998 | Bryant et al. | |
| 5,840,647 A | 11/1998 | Puckette et al. | |
| 6,130,358 A | 10/2000 | Tolleson et al. | |
| 6,265,620 B1 | 7/2001 | Urata et al. | |
| 6,362,354 B1 | 3/2002 | Bunel et al. | |
| 6,437,192 B1 | 8/2002 | Bunel | |
| 6,440,891 B1 | 8/2002 | Maas et al. | |
| 6,906,225 B2 | 6/2005 | Puckette et al. | |
| 6,995,292 B2 | 2/2006 | Tolleson et al. | |
| 2003/0144559 A1 | 7/2003 | Hess et al. | |
| 2007/0112219 A1 | 5/2007 | Ortmann et al. | |
| 2008/0154067 A1 | 6/2008 | Liu et al. | |
| 2009/0171122 A1 | 7/2009 | Liu et al. | |

FOREIGN PATENT DOCUMENTS

| | | |
|---|---|---|
| EP | 0 301 355 A2 | 2/1989 |
| EP | 0 416 321 A1 | 3/1991 |
| JP | 07 216157 | 8/1995 |
| JP | 2000-026355 | 1/2000 |
| JP | 2001-213834 | 8/2001 |
| WO | WO 2006/003431 A1 | 1/2006 |
| WO | WO 2008/088495 A1 | 7/2008 |
| WO | 2009/085161 A1 | 7/2009 |

OTHER PUBLICATIONS

Chandrasekaran et al. The Effect of Very Bulky Groups on the Equilibrium of Penta- Hexa-coordinated Phosphoranes. Phosphorus, Sulfur, and Silicon, 2006, vol. 181, 1493-1511.*
Aubry et al., "The unusual inhibition of a dirhodium tetraphosphine-based bimetallic hydroformylation catalyst by $PPh_3$", C.R. Chimie 5, 2002, pp. 473-480.
Barros et al., "Rhodium catalyzed hydroformylation of conjugated dienes: Remarkable accelerative effect of triphenylphosphine", Catalysis Communications 8, 2007, pp. 747-750.
Claver et al., "Biarylphosphonites: a class of monodentate phosphorus (III) ligands that outperform their chelating analogues in asymmetric hydrogenation catalysis", $29^{th}$ Feb. 2000, Apr. 17, 2000, P.G. Pringle, Chem. Comm., pp. 961-962.
da Silva et al., "Rhodium catalyzed hydroformylation of linalool", Applied Catalysis A: General 309, 2006, pp. 169-176.
Diéguez et al., "High-Pressure Infrared Studies of Rhodium Complexes Containing Thiolate Bridge Ligands under Hydroformylation Conditions", Organometallics 1999, 18, pp. 2107-2115.
Gordon and Ford, The Chemist's Companion, Kinetics and Energetics, 1972, pp. 156-161, John Wiley & Sons, New York.
International Search Report and Written Opinion dated Mar. 26, 2009 for International Application No. PCT/US2008/013774.
International Search Report and Written Opinion dated Apr. 24, 2009 for International Application No. PCT/US2008/013773.
International Search Report and Written Opinion dated May 2, 2008 for International Application No. PCT/US2007/024968.
Jeon et al., "Hydroformylation of Mixed Octenes Using Rhodium=Bulky Phosphonite Complexes with Excellent Catalytic Activity and Stability", The Chemical Society of Japan, 2004, pp. 174-175, vol. 33, No. 2.
Kalck, "Cooperative Effect Between Two Metal Centres in Hydroformylation: Routes Towards Heterobimetallic Catalysts", Polyhedron, vol. 7, No. 22/23, pp. 2441-2450, 1988.
Kamer et al., "Rhodium Phosphite Catalysts", Rhodium Catalyzed Hyrdoformylation, Edited by van Leeuwen et al., Kluwer Academic Publishers, 2000, pp. 35-62.

(Continued)

*Primary Examiner* — Sikarl A Witherspoon
(74) *Attorney, Agent, or Firm* — William K. McGreevey; Bernard J. Graves, Jr.

(57) ABSTRACT

Novel trivalent organophosphite ligands having the structure of general formula (I):

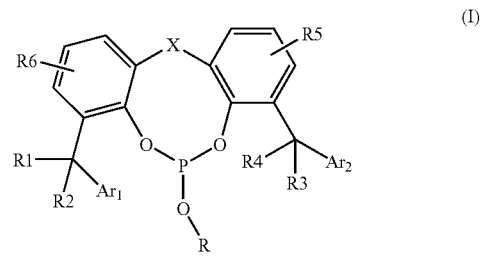

(I)

wherein R is an alkyl or aryl group containing 1 to 30 carbon atoms; $Ar_1$ and $Ar_2$ are aryl groups containing 4 to 30 carbon atoms; R1 to R6 are H or alkyl or aryl hydrocarbon radicals containing 1 to 40 carbon atoms; and X is a connecting group or a simple chemical bond, were developed and found to be very active for hydroformylation processes for ethylenically unsaturated substrates. Catalyst solutions prepared from these ligands with a Rh metal show an unusual "ligand acceleration effect" for simple alkenes, i.e., the hydroformylation activity increases as the concentration of ligand increases, and are capable of producing linear or branched aldehydes under typical hydroformylation conditions.

27 Claims, No Drawings

OTHER PUBLICATIONS

Meyer et al., "Preparation and Single Crystal X-Ray Diffraction Study of Some Fluorophosphites and Phosphite Esters", Z. Naturforsch, Bi. Chem. Sci., 48b, pp. 659-671 (1993).

Notice of Allowance dated Apr. 27, 2009 for U.S. Appl. No. 11/941,217.

Office Action dated Jul. 20, 2007 from U.S. Appl. No. 11/670,628, abandoned.

Office Action dated Sep. 8, 2008 from co-pending U.S. Appl. No. 11/941,217.

Olivier and Booth, "Make Aldehydes by New Oxo Process", Hydrocarbon Processing, Apr. 1970, pp. 112-114.

Puckette, "Halophosphite Ligands for the Rhodium Catalyzed Low-Pressure Hydroformylation Reaction" in "Catalysis of Organic Reactions", Edited by S. R. Schmidt, CRC Press, 2006, pp. 31-38.

Quin, Louis D., "The Common 3-Coordinate Functions", "A Guide to Organophosphorus Chemistry", 2000, pp. 44-91, Chapter 3, Wiley-Interscience.

Selent et al., "Novel Oxyfunctionalized Phosphonite Ligands for the Hydroformylation of Isomeric n-Olefins", Agnew. Chem. Inc., 2000, pp. 1639-1641, 39, No. 9, Wiley-VCH Verlag GmbH, D-69451 Weinheim.

Senderowitz et al., "A Smart Monte Carlo Technique for Free Energy Simulation of Muliconformational Molecules", Journal Am. Soc., 1995, pp. 8211-8219, American Chemical Society.

Smith and March, March's Advanced Organic Chemistry, Free-Energy Differences between Equatorial and Axial Substiuents on a Cyclohexane Ring (A Values), pp. 174-175, 2001, Fifth Edition, John Wiley and Sons, Inc., New York.

Tullock and Coffman, "Synthesis of Fluorides by Metathesis with Sodium Fluoride", J. Org. Chem., vol. 25, pp. 2016-2019, 1960.

U.S. Appl. No. 61/016,665, filed Dec. 26, 2007; Liu et al., now expired.

U.S. Appl. No. 61/016,661, filed Dec. 26, 2007; Liu, now expired.

U.S. Appl. No. 12/330,023, filed Dec. 8, 2008.

U.S. Appl. No. 60/871,158, filed Dec. 21, 2006, Liu et al., now expired.

U.S. Appl. No. 11/670,628, filed Feb. 2, 2007, Liu et al., now abandoned.

van Leeuwen and Roobeek, "Hydroformylation of Less Reactive Olefins with Modified Rhodium Catalysts", Journal of Organometallic Chemistry, 258, 1983, pp. 343-350.

van Leeuwen et al., "Phosphines as ligands; Bite angle effects for diphosphines" in Rhodium Catalyzed Hyrdroformylation, Edited by van Leeuwen et al., Kluwer Academic Publishers, 2000, pp. 63-75.

van Rooy et al., "Bulky Diphosphite-Modified Rhodium Catalysts: Hydroformylation and Characterization", Organometallics, 1996, 15, pp. 835-847.

White et al., "Structural Implications of Nuclear Magnetic Resonance Studies on 1-R-1-Phospha-2,6-dioxacyclohexanes", Journal of the American Chemical Society, 92:24, Dec. 2, 1970, pp. 7125-7135.

Non-Final Office Action date of mailing Oct. 28, 2009 received in co-pending U.S. Appl. No. 12/330,038.

Notice of Allowance and Fees Due date of mailing May 24, 2010 received in co-pending U.S. Appl. No. 12/330,038.

Notice of Allowance and Fees Due date of mailing Jul. 23, 2009 received in co-pending U.S. Appl. No. 12/330,038.

Notice of Allowance and Fees Due date of mailing Jul. 23, 2009 received in co-pending U.S. Appl. No. 12/330,023.

Notice of Allowance and Fees Due date of mailing Nov. 16, 2009 received in co-pending U.S. Appl. No. 12/330,023.

Notice of Allowance and Fees Due date of mailing Mar. 1, 2010 received in co-pending U.S. Appl. No. 12/330,023.

Notice of Allowance and Fees Due date of mailing May 27, 2010 received in co-pending U.S. Appl. No. 12/330,023.

Notification of Transmittal of the International Search Report and the Written Opinion of the International Searching Authority, or the Declaration date of mailing Aug. 9, 2010 received in International Application No. PCT/US10/01642.

* cited by examiner

PHOSPHITE CONTAINING CATALYSTS FOR HYDROFORMYLATION PROCESSES

FIELD OF THE INVENTION

This invention generally relates to phosphite compounds, a catalyst solution containing the same, and a hydroformylation process using the catalyst solution.

BACKGROUND OF THE INVENTION

The hydroformylation reaction, also known as the oxo reaction, is used extensively in commercial processes for the preparation of aldehydes by the reaction of one mole of an olefin with one mole each of hydrogen and carbon monoxide. One use of the reaction is in the preparation of normal- and iso-butyraldehyde from propylene. The ratio of the amount of the normal aldehyde product to the amount of the iso aldehyde product typically is referred to as the normal-to-iso (N:I) or (N/I) or the normal-to-branched (N:B) ratio. In the case of propylene, the normal- and iso-butyraldehydes obtained from propylene are in turn converted into many commercially valuable chemical products such as, for example, n-butanol, 2-ethyl-hexanol, n-butyric acid, iso-butanol, neo-pentyl glycol, 2,2,4-trimethyl-1,3-pentanediol, and the mono-isobutyrate and di-isobutyrate esters of 2,2,4-trimethyl-1,3-pentanediol.

In most cases, a phosphorus ligand-containing catalyst is used for the oxo process (so called "low pressure hydroformylation process"). Phosphorus ligands not only can stabilize metal, but can also regulate the catalyst activity and selectivity. Oxo catalyst activity often decreases as the amount of phosphorus ligands increases while the catalyst stability increases with increasing amounts of ligand. Therefore, there exists an optimum concentration of phosphorus ligands for operating an oxo reactor which is the result of a tradeoff between increased stability and reduced catalyst activity.

In reality, the gradual loss of phosphorus ligands is inevitable because of decomposition and other reasons. In some cases, such as overflow reactors, the decomposition of ligands may be worsened due to the high temperature required to separate catalysts from products. In practice, fresh phosphorus ligands have to be replenished to the reactor on a regular basis to compensate for the loss of ligands.

Thus, there is a need in the art for ligands that not only stabilize the catalyst at higher concentrations, but also can increase the catalyst activity at such concentrations.

SUMMARY OF THE INVENTION

A class of ligands has been discovered that can substantially increase the Rh catalyst activity by simply increasing the novel phosphite ligand concentration. In some embodiments, the ligand offers one or more benefits such as enhanced catalyst stability, increased production rate, and reduced daily operation costs due to eliminated needs for replenishing ligands.

In one aspect, the present invention provides a phosphite compound having the structure of formula (I):

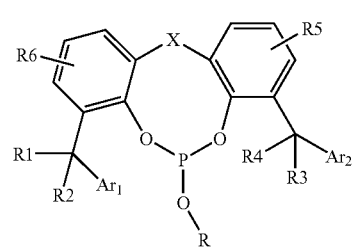

wherein
R is an alkyl or aryl group containing 1 to 30 carbon atoms;
$Ar_1$ and $Ar_2$ are each independently aryl groups containing 4 to 30 carbon atoms;
R1 to R6 are each independently selected from H and hydrocarbyl containing 1 to 40 carbon atoms; and
X is
(i) a chemical bond directly between ring carbon atoms of each aromatic group,
(ii) a heteroatom, or
(iii) a group having the formula

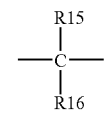

wherein R15 and R16 are each independently selected from hydrogen and alkyl or aryl having up to 10 carbon atoms.

In a second aspect, the present invention provides a catalyst solution comprising:
(a) a phosphite compound; (correct)
(b) a Group VIII metal or rhenium; and
(c) a hydroformylation solvent,
wherein the phosphite compound has the structure of formula (I):

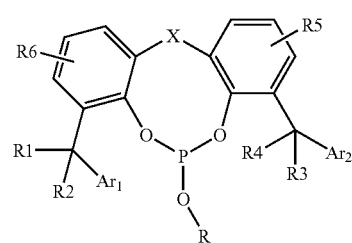

wherein
R is an alkyl or aryl group containing 1 to 30 carbon atoms;
$Ar_1$ and $Ar_2$ are each independently aryl groups containing 4 to 30 carbon atoms;
R1 to R6 are each independently selected from H and hydrocarbyl containing 1 to 40 carbon atoms; and
X is
(i) a chemical bond directly between ring carbon atoms of each aromatic group,
(ii) a heteroatom, or (iii) a group having the formula

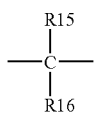

wherein R15 and R16 are each independently selected from hydrogen and alkyl or aryl having up to 10 carbon atoms.

In a third aspect, the present invention provides a process for preparing aldehydes, comprising contacting an olefin with hydrogen and carbon monoxide, under hydroformylation conditions, in the presence of the catalyst solution herein described.

DETAILED DESCRIPTION OF THE INVENTION

New phosphite compounds have been discovered that are useful as ligands in hydroformylation reactions. The invention thus provides new phosphite compounds. The invention further provides highly active catalyst solution for use in hydroformylation reactions.

The catalyst solution comprises:
(a) a phosphite compound;
(b) a Group VIII metal or rhenium; and
(c) a hydroformylation solvent.

The phosphite compound according to the invention has the structure of formula (I):

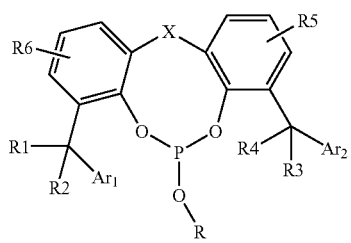

(I)

wherein
R is an alkyl or aryl group containing 1 to 30 carbon atoms;
$Ar_1$ and $Ar_2$ are each independently aryl groups containing 4 to 30 carbon atoms;
R1 to R6 are each independently selected from H and hydrocarbyl containing 1 to 40 carbon atoms; and
X is
(i) a chemical bond directly between ring carbon atoms of each aromatic group,
(ii) a heteroatom, or
(iii) a group having the formula

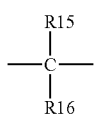

wherein R15 and R16 are each independently selected from hydrogen and alkyl or aryl groups having up to 10 carbon atoms. In some embodiments, R15 and R16 are each independently selected from hydrogen and alkyl groups having one or two carbon atoms. In some embodiments, R15 and R16 are each independently selected from hydrogen and methyl groups. In some embodiments, R15 and R16 are each hydrogen.

The heteroatom can be any atom other than carbon that can form the bonds with the two aryl rings as shown in Formula (I) without compromising the efficacy of the ligand. In some embodiments, the heteroatom is selected from sulfur, oxygen, nitrogen, and silicon, provided that the silicon and nitrogen will have additional substituents bonded thereto to complete the atoms bonding capability. Some examples of substituents which are acceptable include alkyl groups of 1 to 20 carbon atoms and aromatic groups of 6 to 20 carbon atoms. In some embodiments, the heteroatom is selected from O, Si, and N, again, with additional atoms bonded to a Si or N.

R is a hydrocarbyl group selected from unsubstituted and substituted alkyl, cycloalkyl, and aryl groups containing 1 to about 30 carbon atoms. In some embodiments the total carbon content of R is in the range of about 1 to 20 carbon atoms. Examples of the alkyl groups that R can represent include methyl, ethyl, butyl, pentyl, hexyl, 2-ethylhexyl, octyl, decyl, dodecyl, octadecyl and various isomers thereof. The alkyl groups may be substituted, for example, with up to two substituents such as alkoxy, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts, and the like. Cyclopentyl, cyclohexyl and cycloheptyl are examples of the cycloalkyl groups that R can represent. The cycloalkyl groups may be substituted with alkyl or any of the substituents described with respect to the possible substituted alkyl groups. In some embodiments, the unsubstituted or substituted alkyl and cycloalkyl groups that R can represent are alkyls of up to about 8 carbon atoms, benzyl, cyclopentyl, cyclohexyl, and cycloheptyl.

Examples of the aryl groups that R can represent include carbocyclic aryls such as phenyl, naphthyl, anthracenyl, and substituted derivatives thereof. Examples of the carbocyclic aryl groups that R can represent include the radicals having the formulas (II) to (IV):

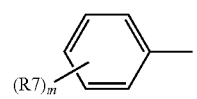

(II)

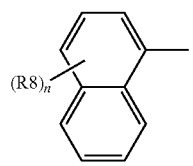

(III)

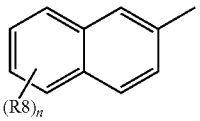

(IV)

wherein R7 and R8 may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, sulfonate salts, and the like. In some embodiments, the alkyl moiety of the aforesaid alkyl, alkoxy, alkanoyl, alkoxycarbonyl, and alkanoyloxy groups contains up to about 8 carbon atoms. Although it is possible for m to represent 0 to 5 and for n to represent 0 to 7, the value of each of m and n will not exceed 2. In some embodiments, R7 and R8 represent lower alkyl groups, i.e., straight-chain and branched-chain alkyl of up to about 4 carbon atoms, and m and n each represent 0, 1, or 2.

The hydrocarbyl groups represented by R1 to R4 are selected from unsubstituted and substituted alkyl, cycloalkyl, and aryl groups containing up to about 40 carbon atoms. In some embodiments, the total carbon content of R1 to R4 is in the range of about 1 to 15 carbon atoms. Examples of the alkyl groups that R1 to R4 can represent include methyl, ethyl, butyl, pentyl, hexyl, 2-ethylhexyl, octyl, decyl, dodecyl, octadecyl, and various isomers thereof. The alkyl groups may be substituted, for example, with up to two substituents such as alkoxy, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts, and the like. Cyclopentyl, cyclohexyl, and cycloheptyl are examples of the cycloalkyl groups that R1 to R4 can represent. The cycloalkyl groups may be substituted with alkyl or any of the substituents described with respect to the possible substituted alkyl groups. In some embodiments, the unsubstituted or substituted alkyl and cycloalkyl groups that R1 to R4 can represent are alkyls of up to about 8 carbon atoms, benzyl, cyclopentyl, cyclohexyl, or cycloheptyl.

Examples of the aryl groups that R1 to R4 can represent include carbocyclic aryl such as phenyl, naphthyl, anthracenyl, and substituted derivatives thereof. Examples of the carbocyclic aryl groups that R1 to R4 can represent include radicals having the formulas (V)-(VII):

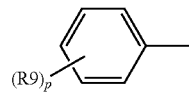

(V)

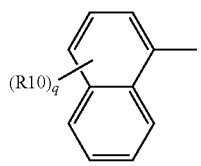

(VI)

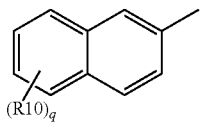

(VII)

wherein R9 and R10 may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, sulfonate salts, and the like. In some embodiments, the alkyl moiety of the aforesaid alkyl, alkoxy, alkanoyl, alkoxycarbonyl, and alkanoyloxy groups contains up to about 8 carbon atoms. Although it is possible for p to represent 0 to 5 and for q to represent 0 to 7, in some embodiments, the value of each of p and q will not exceed 2. In some embodiments, R9 and R10 represent lower alkyl groups, i.e., straight-chain and branched-chain alkyl of up to about 4 carbon atoms, and m and n each represent 0, 1, or 2.

The hydrocarbyl groups represented by R5 and R6 may be the same or different, separate or combined, and are selected from unsubstituted and substituted alkyl, cycloalkyl, and aryl groups containing a total of up to about 40 carbon atoms. In some embodiments, the total carbon content of substituents R5 and R6 is in the range of about 1 to 35 carbon atoms. Examples of the unsubstituted or substituted alkyl groups that R5 and R6 can represent include methyl, ethyl, butyl, pentyl, hexyl, 2-ethylhexyl, octyl, decyl, dodecyl, octadecyl, 1-alkylbenzyl, and various isomers thereof. The alkyl groups may be substituted, for example, with up to two substituents such as alkoxy, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts, and the like. Cyclopentyl, cyclohexyl, and cycloheptyl are examples of the cycloalkyl groups that R5 and R6 individually can represent. The cycloalkyl groups may be substituted with alkyl or any of the substituents described with respect to the possible substituted alkyl groups. In some embodiments the unsubstituted or substituted alkyl and cycloalkyl groups that R5 and R6 can represent are alkyls of up to about 10 carbon atoms such as benzyl, 1-alkylbenzyl, cyclopentyl, cyclohexyl, and cycloheptyl, etc.

Examples of the aryl groups that R5 and R6 can represent include carbocyclic aryl such as phenyl, naphthyl, anthracenyl, and substituted derivatives thereof. Examples of the carbocyclic aryl groups that R5 and R5 can represent include radicals having the formulas (VIII)-(X):

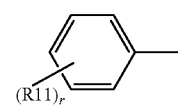

(VIII)

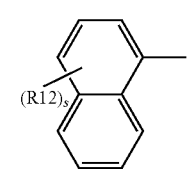

(IX)

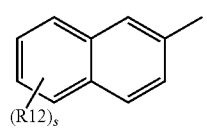

(X)

wherein R11 and R12 may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, sulfonate salts, and the like. In some embodiments, the alkyl moiety of the aforesaid alkyl, alkoxy, alkanoyl, alkoxycarbonyl, and alkanoyloxy groups contains up to about 8 carbon atoms. Although it is possible for r to represent 0 to 5 and for s to represent 0 to 7, in some embodiments, the value of each of r and s will not exceed 2. In some embodiments, R11 and R12 represent lower alkyl groups, i.e., straight-chain and branched-chain alkyl of up to about 10 carbon atoms, and r and s each represent 0, 1, or 2.

In some embodiments, combinations of two groups selected from R1 to R6 may in combination or collectively represent a divalent hydrocarbyl group containing up to about 40 carbon atoms. In some embodiments, the divalent hydrocarbyl group contains from about 12 to 36 carbon atoms. Examples of such divalent groups include alkyl of about 2 to 12 carbon atoms, cyclohexyl, and aryl. Specific examples of the alkyl and cycloalkyl groups include ethylene, trimethylene, 1,3-butanediyl, 2,2-dimethyl-1,3-propanediyl, 1,1,2-triphenylethanediyl, 2,2,4-trimethyl-1,3-pentanediyl, 1,2-cyclohexylene, and the like.

Examples of the aryl groups that $Ar_1$ and $Ar_2$ can individually represent include carbocyclic aryl such as phenyl, naphthyl, anthracenyl, and substituted derivatives thereof. Examples of the carbocyclic aryl groups that $Ar_1$ and $Ar_2$ can represent include radicals having the formulas (XI) to (XIII):

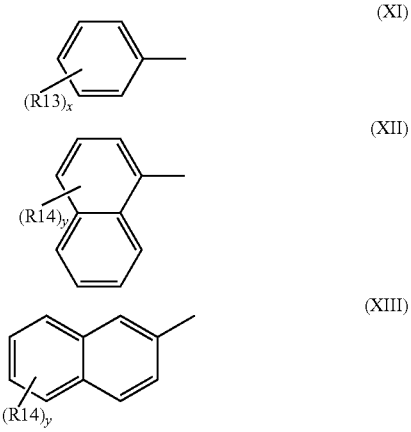

wherein R13 and R14 may represent one or more substituents independently selected from alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, sulfonate salts, and the like. In some embodiments, the alkyl moiety of the aforesaid alkyl, alkoxy, alkanoyl, alkoxycarbonyl, and alkanoyloxy groups contains up to about 8 carbon atoms. Although it is possible for x to represent 0 to 5 and for y to represent 0 to 7, in some embodiments, the value of each of x and y will not exceed 2. In some embodiments, R13 and R14 represent lower alkyl groups, i.e., straight-chain and branched-chain alkyl of up to about 10 carbon atoms, and x and y each represent 0, 1, or 2. In some embodiments, R13 and R14 represent lower alkyl groups, i.e., straight-chain and branched-chain alkyl of up to about 4 carbon atoms, and x and y each represent 0, 1, or 2.

The phosphite compounds of this invention can be prepared by any effective method. A variety of methods for preparing phosphites are reported in "A Guide to Organophosphorus Chemistry", Louis D. Quin, 2000, Wiley-Interscience, pp. 64 et seq. For example, phosphites can be prepared by the reaction of phosphorus trichloride with corresponding phenols and alcohols in the presence of an acid scavenger such as triethylamine. Phosphites can also be made, for example, by trans-esterification reactions such as reaction of trimethyl phosphite with phenols or alcohols.

The novel catalyst systems provided by the present invention comprise a combination of one or more transition metals selected from the Group VIII metals and rhenium and one or more of the phosphite compounds described in detail hereinabove. The transition metal may be provided in the form of various metal compounds such as carboxylate salts of the transition metal. In some embodiments, the metal is rhodium.

Rhodium compounds that may be used as a source of rhodium for the active catalyst include rhodium (II) or rhodium (III) salts of carboxylic acids, examples of which include di-rhodium tetraacetate dihydrate, rhodium(II) acetate, rhodium(II) isobutyrate, rhodium(II) 2-ethylhexanoate, rhodium(II) benzoate, and rhodium(II) octanoate. Also, rhodium carbonyl species such as $Rh_4(CO)_{12}$, $Rh_6(CO)_{16}$, and rhodium(I) acetylacetonate dicarbonyl may be suitable rhodium feeds. Additionally, rhodium organophosphine complexes such as tris(triphenylphosphine) rhodium carbonyl hydride may be used when the phosphine moieties of the complex fed are easily displaced by the phosphite ligands of the present invention. Other rhodium sources include rhodium salts of strong mineral acids such as chlorides, bromides, nitrates, sulfates, phosphates, and the like.

The absolute concentration of rhodium in the reaction mixture or solution may vary from 1 mg/liter up to 5000 mg/liter or more. In some embodiments of this invention, the normal concentration of rhodium in the reaction solution is in the range of about 20 to 300 mg/liter. Concentrations of rhodium lower than this range generally yield lower reaction rates with most olefin reactants and/or require reactor operating temperatures that are so high as to be detrimental to catalyst stability. Concentrations above this range involve higher rhodium costs.

The ratio of gram moles phosphite ligand to gram atoms transition metal can vary over a wide range, e.g., gram mole phosphite:gram atom transition metal ratio of about 1:1 to 500:1. For rhodium-containing catalyst systems, the gram mole phosphite:gram atom rhodium ratio in some embodiments is in the range of about 1:1 to 200:1 with ratios in some embodiments in the range of about 1:1 to 100:1.

No special or unusual techniques are required for preparing the catalyst systems and solutions of the present invention, although in some embodiments a catalyst of high activity is obtained if all manipulations of the rhodium and phosphite ligand components are carried out under an inert atmosphere, e.g., nitrogen, argon, and the like. The desired quantities of a suitable rhodium compound and ligand are charged to the reactor in a suitable solvent. The sequence in which the various catalyst components or reactants are charged to the reactor is not critical.

The hydroformylation reaction solvent may be selected from a wide variety of compounds, mixture of compounds, or materials that are liquid at the pressure at which the process is being operated. Such compounds and materials include various alkanes, cycloalkanes, alkenes, cycloalkenes, carbocyclic aromatic compounds, alcohols, esters, ketones, acetals, ethers, and water. Specific examples of such solvents include alkane and cycloalkanes such as dodecane, decalin, octane, iso-octane mixtures, cyclohexane, cyclooctane, cyclododecane, methylcyclohexane; aromatic hydrocarbons such as benzene, toluene, xylene isomers, tetralin, cumene, alkyl-substituted aromatic compounds such as the isomers of diisopropylbenzene, triisopropylbenzene and tert-butylbenzene; alkenes and cycloalkenes such as 1,7-octadiene, dicyclopentadiene, 1,5-cyclooctadiene, octene-1, octene-2,4-vinylcyclohexene, cyclohexene, 1,5,9-cyclododecatriene, 1-pentene; crude hydrocarbon mixtures such as naphtha, mineral oils and kerosene; and high-boiling esters such as 2,2,4-trimethyl-1, 3-pentanediol diisobutyrate. The aldehyde product of the hydroformylation process may also be used.

In some embodiments, the solvent is the higher boiling by-products that are naturally formed during the process of the hydroformylation reaction and the subsequent steps, e.g., distillations, that may be required for aldehyde product isolation. The main criterion for the solvent is that it dissolves the catalyst and olefin substrate and does not act as a poison to the catalyst. Some examples of solvents for the production of volatile aldehydes, e.g., butyraldehydes, are those that are sufficiently high boiling to remain, for the most part, in a gas sparged reactor. Some examples of solvents and solvent combinations that are in the production of less volatile and non-volatile aldehyde products include 1-methyl-2-pyrrolidinone, dimethyl-formamide, perfluorinated solvents such as perfluoro-kerosene, sulfolane, water, and high boiling hydrocarbon liquids as well as combinations of these solvents. Non-hydroxylic compounds, in general, and hydrocarbons, in particular, may be used advantageously as the hydroformylation solvent since their use can minimize decomposition of the phosphite ligands.

In another aspect, the present invention provides a process for preparing aldehydes, comprising contacting an olefin with hydrogen and carbon monoxide, under hydroformylation conditions, in the presence of the catalyst solution herein described.

The reaction conditions for the process of the present invention can be conventional hydroformylation conditions. The process may be carried out at temperatures in the range of about 20° to 200° C., in some embodiments, the hydroformylation reaction temperatures are from 50° to 135° C. In some embodiments, reaction temperatures range from 75° to 125° C. Higher reactor temperatures can increase the rate of catalyst decomposition while lower reactor temperatures can result in relatively slow reaction rates. The total reaction pressure may range from about ambient or atmospheric up to 70 bars absolute (about 1000 psig). In some embodiments, pressure ranges from about 8 to 28 bars absolute (about 100 to 400 psig).

The hydrogen:carbon monoxide mole ratio in the reactor likewise may vary considerably ranging from 10:1 to 1:10, and the sum of the absolute partial pressures of hydrogen and carbon monoxide may range from 0.3 to 36 bars absolute. The partial pressures of the ratio of the hydrogen to carbon monoxide in the feed can be selected according to the linear: branched isomer ratio desired. Generally, the partial pressure of hydrogen and carbon monoxide in the reactor can be maintained within the range of about 1.4 to 13.8 bars absolute (about 20 to 200 psia) for each gas. The partial pressure of carbon monoxide in the reactor can be maintained within the range of about 1.4 to 13.8 bars absolute (about 20 to 200 psia) and can be varied independently of the hydrogen partial pressure. The molar ratio of hydrogen to carbon monoxide can be varied widely within these partial pressure ranges for the hydrogen and carbon monoxide. The ratios of hydrogen-to-carbon monoxide and the partial pressure of each in the synthesis gas (syn gas—carbon monoxide and hydrogen) can be readily changed by the addition of either hydrogen or carbon monoxide to the syn gas stream. With the phosphite ligands described herein, the ratio of linear to branched products can be varied widely by changing the partial pressures of the carbon monoxide in the reactor.

Any of the known hydroformylation reactor designs or configurations such as overflow reactors and vapor take-off reactors may be used in carrying out the process provided by the present invention. Thus, a gas-sparged, vapor take-off reactor design as disclosed in the examples set forth herein may be used. In this mode of operation, the catalyst which is dissolved in a high boiling organic solvent under pressure does not leave the reaction zone with the aldehyde product taken overhead by the unreacted gases. The overhead gases then are chilled in a vapor/liquid separator to liquefy the aldehyde product and the gases can be recycled to the reactor. The liquid product is let down to atmospheric pressure for separation and purification by conventional technique. The process also may be practiced in a batchwise manner by contacting the olefin, hydrogen and carbon monoxide with the present catalyst in an autoclave.

A reactor design where catalyst and feedstock are pumped into a reactor and allowed to overflow with product aldehyde, i.e. liquid overflow reactor design, is also suitable. For example, high boiling aldehyde products such as nonyl aldehydes may be prepared in a continuous manner with the aldehyde product being removed from the reactor zone as a liquid in combination with the catalyst. The aldehyde product may be separated from the catalyst by conventional means such as by distillation or extraction, and the catalyst then recycled back to the reactor. Water soluble aldehyde products, such as hydroxy butyraldehyde products obtained by the hydroformylation of allyl alcohol, can be separated from the catalyst by extraction techniques. A trickle-bed reactor design is also suitable for this process. It will be apparent to those skilled in the art that other reactor schemes may be used with this invention.

The olefin used as the starting material for this invention is not particularly limiting. Specifically, the olefin can be ethylene, propylene, butene, pentene, hexene, octene, styrene, non-conjugated dienes such as 1,5-hexadiene, and blends of these olefins. Furthermore, the olefin may be substituted with functional groups so long as they do not interfere with the hydroformylation reaction. Suitable substituents on the olefin include any functional group that does not interfere with the hydroformylation reaction and includes groups such as carboxylic acids and derivatives thereof such as esters and amides, alcohols, nitriles, and ethers. Examples of substituted olefins include esters such as methyl acrylate or methyl oleate, alcohols such as allyl alcohol and 1-hydroxy-2,7-octadiene, and nitriles such as acrylonitrile.

The amount of olefin present in the reaction mixture can also vary. For example, relatively high-boiling olefins such as 1-octene may function both as the olefin reactant and the process solvent. In the hydroformylation of a gaseous olefin feedstock such as propylene, the partial pressures in the vapor space in the reactor in some embodiments are in the range of about 0.07 to 35 bars absolute. The rate of reaction can be favored by high concentrations of olefin in the reactor. In the hydroformylation of propylene, the partial pressure of propylene in some embodiments is greater than 1.4 bars, e.g., from about 1.4 to 10 bars absolute. In the case of ethylene hydroformylation, the partial pressure of ethylene in the reactor in some embodiments is greater than 0.14 bars absolute.

This invention can be further illustrated by the following examples of embodiments thereof, although it will be understood that these examples are included merely for purposes of illustration and are not intended to limit the scope of the invention. Unless otherwise indicated, all percentages are by weight. As used throughout this application, the reference to a molecule or moiety as being "substituted" means that the molecule or moiety contains one or more substituent in place of where a hydrogen atom would be on the molecule or moiety identified. Thus, a "substituted" aryl molecule having alkyl substituents would include, for example, an alkylbenzene such as toluene.

EXAMPLES

Synthesis of Phosphite Ligands

The preparation of the phosphite ligands was accomplished by sequential reaction of the bisphenol with phosphorus trichloride and the appropriate alcohol or phenol. The bisphenol precursors for all ligands were all prepared by literature procedures (Casiraghi, et al., Synthesis (1981) 143) or by simple modifications thereof. All of the phosphites were isolated as white crystalline solids although no particular effort was made to rigorously purify the ligands.

Ligand A

Ligand A, 6-methoxy-2,4,8,10-tetramethyl-12H-dibenzo[d,g][1,3,2]dioxaphosphocine, having the structure shown below, was prepared.

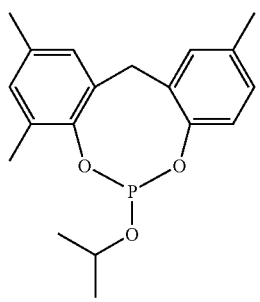

A

Ligand A was prepared by combining 6,6'-methylenebis(2,4-dimethylphenol) (10.9 grams, 40 millimole), tetrabutyl ammonium bromide (0.25 grams), and toluene (200 milliliters) in a round bottom flask equipped for simple distillation. Approximately 50 milliliters of toluene was distilled from the mixture to azeotropically dry the mixture. The flask was cooled to a safe handling temperature and equipped with an addition funnel, a condenser and a $N_2$ source with the excess $N_2$ vented to the back of a fume hood. The flask was cooled with an external ice water bath and then phosphorus trichloride (5.8 grams. 42.0 millimole) was added with stirring. The reaction was stirred 0.5 hour and then heated to reflux for 2 hours. The flask was then cooled to a safe handling temperature, equipped for simple distillation and about 75 milliliters of toluene and the excess $PCl_3$ was removed by distillation. The flask was returned to the ice water bath and then a mixture of triethylamine (5.05 grams, 50.0 millimole) and isopropanol (2.7 grams, 45 millimole) was added drop wise with stirring. The reaction was followed by gas chromatography and upon completion of the reaction, 50 milliliters of dry hexane was added and the precipitated solids were removed by distillation under a dry $N_2$ atmosphere. The filtrate was passed through a 1 inch diameter by 2 inch height column of basic alumina and the column rinsed with toluene. The organic solvents were removed to give the product which crystallized upon standing to give 11.78 grams of a white solid.

Spectroscopic data of Ligand A: $^{31}P$ NMR ($CDCl_3$): 130.9 ppm (s).

Liqand B

Ligand B, 6-methoxy-2,4,8,10-tetrakis(2-phenylpropan-2-yl)-12H-dibenzo[d,g][1,3,2]dioxaphosphocine, having the structure shown below, was synthesized using the stoichiometric ratios and conditions illustrated by the procedure for the preparation of Ligand A, except that the bisphenol was 6,6'-methylenebis(2,4-bis(2-phenylpropan-2-yl)phenol) and the alcohol was methanol.

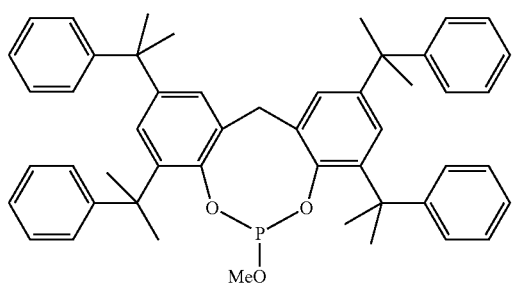

B

Spectroscopic data of Ligand B: $^{31}P$ NMR ($CDCl_3$): 125.8 ppm (s).

Liqand C

Ligand C, 6-isopropoxy-2,4,8,10-tetrakis(2-phenylpropan-2-yl)-12H-dibenzo[d,g][1,3,2]dioxaphocine, having the structure shown below, was synthesized using the stoichiometric ratios and conditions illustrated by the procedure for the preparation of Ligand A, except that the bisphenol was 6,6'-methylenebis(2,4-bis(2-phenylpropan-2-yl)phenol) and the alcohol was isopropanol.

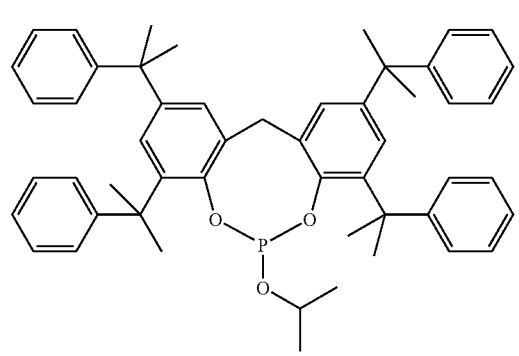

C

Spectroscopic data of Ligand C: $^{31}P$ NMR ($CDCl_3$): 126.5 ppm (s).

Liqand D

Ligand D, 6-(benzyloxy)-2,4,8,10-tetrakis(2-phenylpropan-2-yl)-12H-dibenzo[d,g][1,3,2]dioxaphosphocine, having the structure shown below, was using the stoichiometric ratios and conditions illustrated by the procedure for the preparation of Ligand A, except that the bisphenol was 6,6'-methylenebis(2,4-bis(2-phenylpropan-2-yl)phenol) and the alcohol was benzyl alcohol.

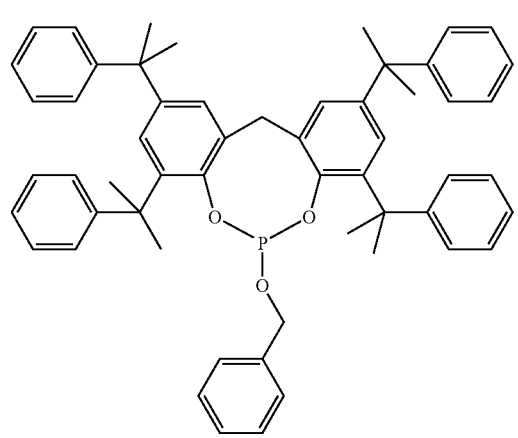

D

Spectroscopic data of Ligand D: $^{31}P$ NMR ($CDCl_3$): 125.2 ppm (s).

Liqand E

Ligand E, 2,4,8,10-tetrakis(2-phenylpropan-2-yl)-6-(p-tolyloxy)-12H-dibenzo[d,g][1,3,2]dioxaphosphocine, having the structure shown below, was using the stoichiometric ratios and conditions illustrated by the procedure for the preparation of Ligand A, except that the bisphenol was 6,6'-methylenebis(2,4-bis(2-phenylpropan-2-yl)phenol) and the hydroxylic compound was 4-methylphenol.

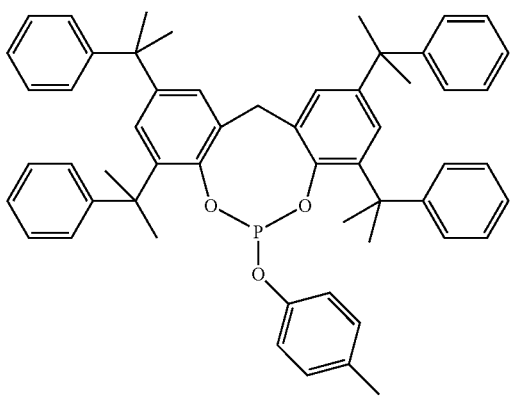

E

Spectroscopic data of Ligand E: $^{31}$P NMR (CDCl$_3$): 122.9 ppm (s).

Liqand F

Ligand F, 6-(3,5-dimethylphenoxy)-2,4,8,10-tetrakis(2-phenylpropan-2-yl)-12H-dibenzo[d,g][1,3,2]dioxaphosphocine, having the structure shown below, was synthesized using the stoichiometric ratios and conditions illustrated by the procedure for the preparation of Ligand A, except that the bisphenol was 6,6'-methylenebis(2,4-bis(2-phenylpropan-2-yl)phenol) and the hydroxylic compound was 3,5-dimethylphenol.

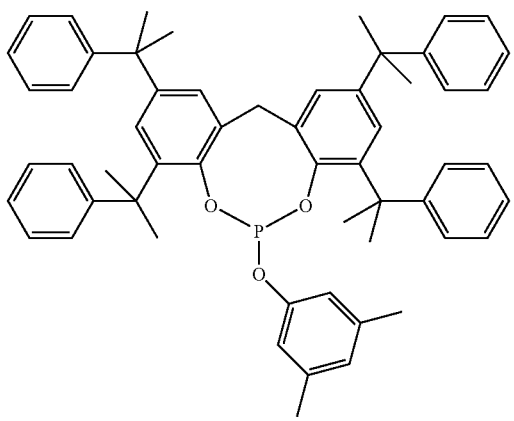

F

Spectroscopic data of Ligand F: $^{31}$P NMR (CDCl$_3$): 123.5 ppm (s).

Hydroformylation Process Set-Up

The hydroformylation process in which propylene is allowed to react with hydrogen and carbon monoxide to produce butyraldehydes was carried out in a vapor take-off reactor made up of a vertically arranged stainless steel pipe having a 2.5 cm inside diameter and a length of 1.2 meters. The reactor was encased in an external jacket that was connected to a hot oil machine. The reactor had a filter element welded into the side down near the bottom of the reactor for the inlet of gaseous reactants. The reactor contained a thermocouple which was arranged axially with the reactor in its center for accurate measurement of the temperature of the hydroformylation reaction mixture. The bottom of the reactor had a high pressure tubing connection that was connected to a cross. One of the connections to the cross permitted the addition of non-gaseous reactants such as higher boiling alkenes or make-up solvents, another led to the high-pressure connection of a differential pressure (D/P) cell that was used to measure catalyst level in the reactor and the bottom connection was used for draining the catalyst solution at the end of the run.

In the hydroformylation of propylene in a vapor take-off mode of operation, the hydroformylation reaction mixture or solution containing the catalyst was sparged under pressure with the incoming reactants of propylene, hydrogen and carbon monoxide as well as any inert feed such as nitrogen. As butyraldehyde was formed in the catalyst solution, it and unreacted reactant gases were removed as a vapor from the top of the reactor by a side-port. The vapor removed was chilled in a high-pressure separator where the butyraldehyde product was condensed along with some of the unreacted propylene. The uncondensed gases were let down to atmospheric pressure via the pressure control valve. These gases passed through a series of dry-ice traps where any other aldehyde product was collected. The product from the high-pressure separator was combined with that of the traps, and was subsequently weighed and analyzed by standard gas/liquid phase chromatography (GC/LC) techniques for the net weight and normal/iso ratio of the butyraldehyde product. Activity was calculated as kilograms of butyraldehydes produced per gram of rhodium per hour.

The gaseous feeds to the reactor were fed to the reactor via twin cylinder manifolds and high-pressure regulators. The hydrogen passed through a mass flow controller and then through a commercially available "Deoxo" (registered trademark of Engelhard Inc.) catalyst bed to remove any oxygen contamination. The carbon monoxide passed through an iron carbonyl removal bed (as disclosed in U.S. Pat. No. 4,608,239), a similar "Deoxo" bed heated to 125° C., and then a mass flow controller. Nitrogen can be added to the feed mixture as an inert gas. Nitrogen, when added, was metered in and then mixed with the hydrogen feed prior to the hydrogen Deoxo bed. Propylene was fed to the reactor from feed tanks that were pressurized with hydrogen and was controlled using a liquid mass flow meter. All gases and propylene were passed through a preheater to ensure complete vaporization of the liquid propylene prior to entering the reactor.

Reaction Procedure

The following procedures were used to prepare ligands except where otherwise noted. A catalyst solution was prepared under nitrogen using a charge of 7.7 mg of rhodium (0.075 mmol, as rhodium 2-ethylhexanoate) various amounts of the ligand as indicated in Table 1; 20 ml of normal butyraldehyde; and 190 ml of Texanol® (2,2,4-trimethylpentane-1,3-diol monoisobutyrate). The mixture was stirred under nitrogen until a homogeneous solution was obtained (heated if necessary).

The mixture was charged to the reactor in a manner described previously and the reactor sealed. The reactor pressure control was set at 17.9 bar (260 psig), and the external oil jacket on the reactor was heated to 85° C. Hydrogen, carbon monoxide, nitrogen, and propylene vapors were fed through the frit at the base of the reactor, and the reactor was allowed to build pressure. The hydrogen and carbon monoxide (H$_2$/CO ratio was set to be 1:1) were fed to the reactor at a rate of 6.8 liters/min and the nitrogen feed was set at 1.0 liter/min. The propylene was metered as a liquid and fed at a rate of 1.89 liters/min (212 grams/hour). The temperature of the external oil was modified to maintain an internal reactor temperature of 95° C. The unit was operated for 5 hours and hourly samples taken. The hourly samples were analyzed as described above using a standard GC method. The last three samples were used to determine the N/I ratio and catalyst activity. The foregoing procedures were conducted for the ligands listed below.

Comparative Examples 1-3 (Fluorophosphite Ligand)

Comparative Examples 1-3 and the procedures and data regarding those examples were copied directly from Puckette, "Halophosphite Ligands for the Rhodium Catalyzed Low-Pressure Hydroformylation Reaction" by Puckette, T. A., in "Catalysis of Organic Reactions", Edited by S. R. Schmidt, CRC Press (2006), pp. 31-38, to illustrate that hydroformylation activity decreases as the molar ratio of ligand to Rh increases (the concentration of ligand increases). The ligand described in this literature is a fluorophosphite (Ethanox 398™, 2,2'-ethylidenebis(4,6-di-tert-butylphenyl) fluorophosphite).

As the reference indicates, those reactions were conducted at 260 psig, 115° C., 1:1 H2/CO, 54 psia $C_3H_6$, and 190 mL of bis-2-ethylhexylphthalate solvent (DOP) with different amounts of ligand. The data is presented in Table 1 below and catalyst activity is expressed as kilograms of butyraldehyde per gram Rh per hour. The reaction conditions and the results of this work are presented in Table 1.

Comparative Examples 4-6 (Ligand A)

These examples illustrate that a non-preferred, regular phosphite (Ligand A) also shows a typical relationship between hydroformylation activity and the molar ratio of ligand to Rh, i.e., the aldehydes production rate decreases as the ligand concentration increases. The reaction conditions and the results of this work are presented in Table 1.

Examples 7-9 (Liqand B)

These examples illustrate a desirable nature of phosphite Ligand B. Hydroformylation experiments were carried out in the same manner as Comparative Examples 4-6, except utilizing various amounts of Ligand "B". The reaction conditions and the results of this work are presented in Table 1.

Examples 10-12 (Ligand C)

These examples illustrate a desirable nature of phosphite Ligand C. Hydroformylation experiments were carried out in the same manner as Comparative Examples 4-6, except utilizing various amounts of Ligand "C". The reaction conditions and the results of this work are presented in Table 1.

Examples 13 to 15 (Liqand D)

These examples illustrate a desirable nature of phosphite Ligand D. Hydroformylation experiments were carried out in the same manner as Comparative Examples 4-6, except utilizing various amounts of Ligand "D". The reaction conditions and the results of this work are presented in Table 1.

Examples 16 to 18 (Ligand E)

These examples illustrate a desirable nature of phosphite Ligand E. Hydroformylation experiments were carried out in the same manner as Comparative Examples 4-6, except utilizing various amounts of Ligand "E". The reaction conditions and the results of this work are presented in Table 1.

Examples 19 to 21 (Liqand F)

These examples illustrate a desirable nature of phosphite Ligand F. Hydroformylation experiments were carried out in the same manner as Comparative Examples 4-6, except utilizing various amounts of Ligand "F". The reaction conditions and the results of this work are presented in Table 1.

The reaction conditions and the results of the above work are presented in Table 1.

TABLE 1

Effects of Ligand to Rhodium Molar Ratio on Activity and Selectivity

| Examples | Ligand | Temp ° C. | H2/CO ratio | Ligand to Rh Molar ratio | N/I Ratio | Catalyst Activity* |
|---|---|---|---|---|---|---|
| C-1 | fluorophosphite | 115 | 1:1 | 14:1 | 1.4 | 15.7 |
| C-2 | fluorophosphite | 115 | 1:1 | 30:1 | 3.1 | 6.6 |
| C-3 | fluorophosphite | 115 | 1:1 | 50:1 | 3.8 | 3.3 |
| C-4 | A | 95 | 1:1 | 15:1 | 2.19 | 3.7 |
| C-5 | A | 95 | 1:1 | 25:1 | 2.55 | 1.9 |
| C-6 | A | 95 | 1:1 | 40:1 | 3.28 | 0.8 |
| 7 | B | 95 | 1:1 | 15:1 | 1.31 | 4.1 |
| 8 | B | 95 | 1:1 | 25:1 | 1.26 | 6.5 |
| 9 | B | 95 | 1:1 | 40:1 | 1.27 | 8.8 |
| 10 | C | 95 | 1:1 | 15:1 | 1.73 | 0.8 |
| 11 | C | 95 | 1:1 | 25:1 | 1.47 | 2.1 |
| 12 | C | 95 | 1:1 | 40:1 | 1.43 | 3.1 |
| 13 | D | 95 | 1:1 | 15:1 | 1.42 | 2.7 |
| 14 | D | 95 | 1:1 | 25:1 | 1.35 | 3.9 |
| 15 | D | 95 | 1:1 | 40:1 | 1.33 | 5.3 |
| 16 | E | 95 | 1:1 | 15:1 | 1.03 | 3.5 |
| 17 | E | 95 | 1:1 | 25:1 | 1.00 | 5.4 |
| 18 | E | 95 | 1:1 | 40:1 | 0.98 | 7.9 |
| 19 | F | 95 | 1:1 | 15:1 | 1.15 | 5.2 |
| 20 | F | 95 | 1:1 | 25:1 | 1.04 | 4.7 |
| 21 | F | 95 | 1:1 | 40:1 | 1.03 | 8.2 |

*Activity was determined as kilograms of butyraldehydes produced per gram of rhodium per hour. All examples were done using 0.075 mmol of Rh.

Comparative Examples 1 through 3 illustrate that the hydroformylation reaction activity, under the same reaction temperature and pressure, steadily decreased from 15.7 to 3.3, and the N/I ratio steadily increased from 1.4 to 3.8 when the Ligand/Rh molar ratio increased from 14:1 to 50:1.

Comparative Examples 4 through 6 again illustrate the typical, conventional behavior of a phosphite ligand. While holding reaction temperature and pressure constant, hydroformylation activity steadily decreased from 3.7 to 0.8, and the N/I ratio steadily increased from 2.19 to 3.28 when the Ligand/Rh molar ratio increased from 15:1 to 40:1

Examples 7 through 9 illustrate the desirable nature of Ligand "B". Example 7 showed an activity of 4.1 and an N/I value of 1.31 for a 15:1 Ligand/Rh ratio. As the ratio of Ligand/Rh increased to 25:1 under the same reaction temperature and pressure, the activity increased to 6.5, and the N/I ratio decreased to 1.26 (Example 8). The hydroformylation activity increased to 8.8 when the Ligand to Rh ratio increased to 40:1 (Example 9).

Examples 10 through 12 illustrate the desirable nature of Ligand "C". When the Ligand/Rh ratio increased from 15:1 to 25:1 then 40:1, the activity increased from 0.8 to 2.1 to 3.1, and the N/I value measured were 1.73, then 1.47, then 1.43 under the same reaction temperature and pressure.

Examples 13 through 15 illustrate the desirable nature of Ligand "D". When the Ligand/Rh ratio increased from 15:1 to 40:1, the activity increased from 2.7 to 5.3, and the N/I value decreased from 1.42 to 1.33 under the same reaction temperature and pressure.

Examples 16 through 18 illustrate the desirable nature of Ligand "E". When the Ligand/Rh ratio increased from 15:1 to 40:1, the activity increased from 3.5 to 7.9, and the N/I value decreased from 1.03 to 0.98 under the same reaction temperature and pressure.

Examples 19 through 21 illustrate the desirable nature of Ligand "F". When the Ligand/Rh ratio increased from 15:1 to 40:1, the activity increased from 5.2 to 8.2 (although 4.7 was measured for 25:1) and the N/I value decreased from 1.15 to 1.03 under the same reaction temperature and pressure.

The invention has been described in detail with particular reference to preferred embodiments and illustrative examples thereof, but it will be understood that variations and modifications can be effected within the spirit and scope of the invention.

What is claimed is:

1. A catalyst solution comprising:
   (a) a phosphite compound;
   (b) a Group VIII metal or rhenium; and
   (c) a hydroformylation solvent,
wherein said phosphite compound has the structure of formula (I):

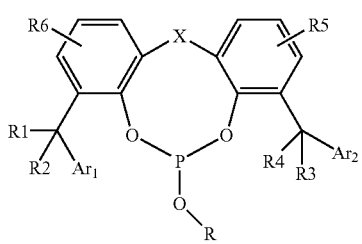

(I)

wherein
   R is an alkyl, cycloalkyl or aryl group which is substituted or unsubstituted and which contains 1 to 30 carbon atoms;
   $Ar_1$ and $Ar_2$ are each independently aryl groups which is substituted or unsubstituted and which contain 4 to 30 carbon atoms;
   R1 to R6 are each independently selected from H and substituted or unsubstituted alkyl, cycloalkyl, and aryl groups containing 1 to 40 carbon atoms; and
   X is
      (i) a chemical bond directly between ring carbon atoms of each aromatic group,
      (ii) a heteroatom, or
      (iii) a group having the formula

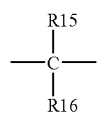

wherein R15 and R16 are each independently selected from hydrogen and alkyl or aryl having one to 10 carbon atoms.

2. The catalyst solution according to claim 1, wherein $Ar_1$ and $Ar_2$ are each independently selected from aryl groups having the structure of formulas (XI)-(XIII):

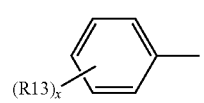

(XI)

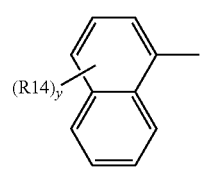

(XII)

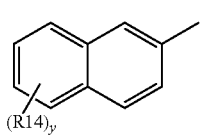

(XIII)

wherein
   R13 and R14 are independently selected from alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, and sulfonate salts;
   x is an integer from 0 to 5; and
   y is an integer from 0 to 7.

3. The catalyst solution according to claim 2, wherein R13 and R14 are independently selected from alkyl having 1 to 10 carbon atoms, and x and y are independently 0, 1, or 2.

4. The catalyst solution according to claim 1, wherein the phosphite compound has the following structure E

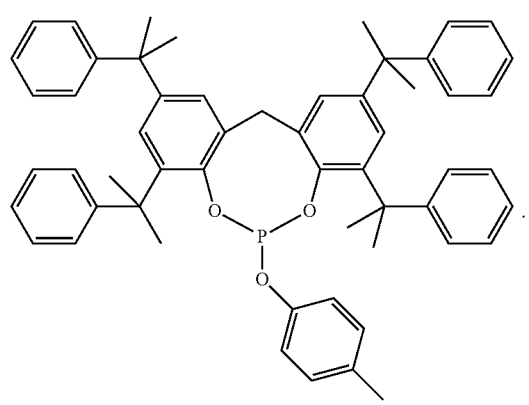

E

5. The catalyst solution according to claim 1, wherein the Group VIII metal is rhodium.

6. The catalyst solution according to claim 5, which comprises from about 20 to 300 mg/l of rhodium, and a ratio of gram moles of phosphite to gram atom of rhodium of about 1:1 to 200:1.

7. The catalyst solution according to claim 4, wherein the Group VIII metal is rhodium.

8. The catalyst solution according to claim 7, which comprises from about 20 to 300 mg/l of rhodium, and a ratio of gram moles of phosphite to gram atom of rhodium of about 1:1 to 200:1.

9. The catalyst solution according to claim 1, wherein the hydroformylation solvent is selected from alkanes, cycloalkanes, alkenes, cycloalkenes, alcohols, esters, ketones, acetals, ethers, aldehydes, water, and mixtures thereof.

10. A process for preparing aldehydes, comprising contacting an olefin with hydrogen and carbon monoxide, under hydroformylation conditions, in the presence of the catalyst solution according to claim 1.

11. The process according to claim 10, wherein $Ar_1$ and $Ar_2$ are each independently selected from aryl groups having the structure of formulas (XI)-(XIII):

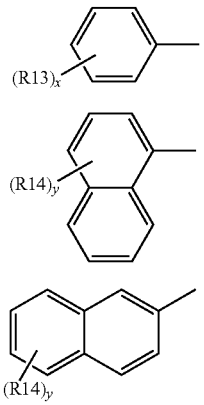

wherein
R13 and R14 are independently selected from alkyl, alkoxy, halogen, cycloalkoxy, formyl, alkanoyl, cycloalkyl, aryl, aryloxy, aroyl, carboxyl, carboxylate salts, alkoxy-carbonyl, alkanoyloxy, cyano, sulfonic acid, and sulfonate salts;
x is an integer from 0 to 5; and
y is an integer from 0 to 7.

12. The process according to claim 11, wherein R13 and R14 are independently selected from alkyl having 1 to 10 carbon atoms, and x and y are independently 0, 1, or 2.

13. The process according to claim 10, wherein the phosphite compound has the following structure E:

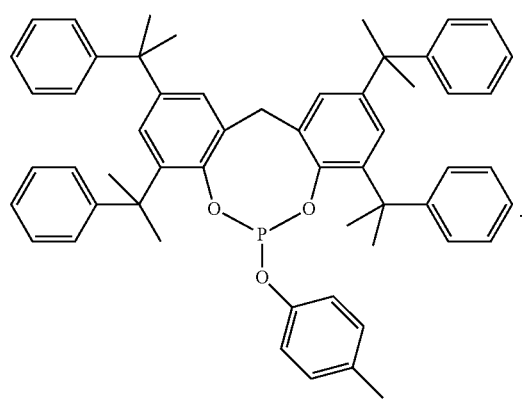

14. The process according to claim 10, wherein the Group VIII metal is rhodium.

15. The process according to claim 14, wherein the catalyst solution comprises from about 20 to 300 mg/l of rhodium, and a ratio of gram moles of phosphite to gram atom of rhodium of about 1:1 to 200:1.

16. The process according to claim 13, wherein the Group VIII metal is rhodium.

17. The process according to claim 16, wherein the catalyst solution comprises from about 20 to 300 mg/l of rhodium, and a ratio of gram moles of phosphite to gram atom of rhodium of about 1:1 to 200:1.

18. The process according to claim 10, wherein the hydroformylation solvent is selected from alkanes, cycloalkanes, alkenes, cycloalkenes, alcohols, esters, ketones, acetals, ethers, aldehydes, water, and mixtures thereof.

19. The process according to claim 10, wherein the hydroformylation conditions comprise a temperature ranging from 75 to 125° C. and a pressure from atmospheric to 70 bars absolute (about 15 to 1,000 psig).

20. The process according to claim 10, wherein the olefin is propylene, and the aldehydes comprise normal- and iso-butyraldehyde.

21. The process according to claim 13, wherein the olefin is propylene, and the aldehydes comprise normal- and iso-butyraldehyde.

22. The catalyst solution according to claim 1, wherein R5 and R6 are each independently selected from substituted or unsubstituted cycloalkyl, aryl-substituted alkyl, and substituted or unsubstituted aryl groups, and R5 and R6 each contain up to 40 carbon atoms.

23. The catalyst solution according to claim 22, wherein the heteroatom is selected from oxygen, silicon, and nitrogen, wherein, if the heteroatom is silicon or nitrogen, the heteroatom has additional substituents bonded thereto to complete the heteroatom's bonding capability.

24. The catalyst solution according to claim 1, wherein the heteroatom is selected from oxygen, silicon, and nitrogen, wherein, if the heteroatom is silicon or nitrogen, the heteroatom has additional substituents bonded thereto to complete the heteroatom's bonding capability.

25. The process according to claim 10, wherein R5 and R6 are each independently selected from substituted or unsubstituted cycloalkyl, aryl-substituted alkyl, and substituted or unsubstituted aryl groups, and R5 and R6 each contain up to 40 carbon atoms.

26. The process according to claim 25, wherein the heteroatom is selected from oxygen, silicon, and nitrogen, wherein, if the heteroatom is silicon or nitrogen, the heteroatom has additional substituents bonded thereto to complete the heteroatom's bonding capability.

27. The process according to claim 10, wherein the heteroatom is selected from oxygen, silicon, and nitrogen, wherein, if the heteroatom is silicon or nitrogen, the heteroatom has additional substituents bonded thereto to complete the heteroatom's bonding capability.

* * * * *